(12) United States Patent
Dehghan Marvast et al.

(10) Patent No.: US 11,471,240 B2
(45) Date of Patent: Oct. 18, 2022

(54) ADAPTIVE PLANNING AND DELIVERY OF HIGH DOSE RATE BRACHYTHERAPY

(71) Applicant: KONINKLIJKE PHILIPS N.V., Eindhoven (NL)

(72) Inventors: Ehsan Dehghan Marvast, New York, NY (US); Shyam Bharat, Arlington, MA (US); Jochen Kruecker, Washington, DC (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 231 days.

(21) Appl. No.: 15/534,016

(22) PCT Filed: Dec. 8, 2015

(86) PCT No.: PCT/IB2015/059429
§ 371 (c)(1),
(2) Date: Jun. 8, 2017

(87) PCT Pub. No.: WO2016/092463
PCT Pub. Date: Jun. 16, 2016

(65) Prior Publication Data
US 2018/0333217 A1 Nov. 22, 2018

Related U.S. Application Data

(60) Provisional application No. 62/090,536, filed on Dec. 11, 2014.

(51) Int. Cl.
*A61B 90/00* (2016.01)
*A61B 34/10* (2016.01)
(Continued)

(52) U.S. Cl.
CPC .............. *A61B 90/06* (2016.02); *A61B 34/10* (2016.02); *A61N 5/1027* (2013.01);
(Continued)

(58) Field of Classification Search
CPC .... A61B 2034/2051; A61B 2034/2055; A61B 2034/2061; A61B 2034/2065;
(Continued)

(56) References Cited

U.S. PATENT DOCUMENTS 6,200,255 B1 * 3/2001 Yu .................... A61N 5/1031
600/1
7,494,457 B2 2/2009 Winkler
(Continued)

FOREIGN PATENT DOCUMENTS

EP 2664359 A1 11/2013
WO WO2011080606 * 7/2011 ............ A61N 5/10
(Continued)

OTHER PUBLICATIONS

Polo (Image fusion techniques in permanent seed implantation, J Contemp Brachyther 2010; 2, 3: 98-106) (Year: 2010).*
(Continued)

*Primary Examiner* — Yi-Shan Yang
*Assistant Examiner* — Alexei Bykhovski
(74) *Attorney, Agent, or Firm* — Sherry Austin

(57) ABSTRACT

A system for dynamic localization of medical instruments includes an ultrasound imaging system (110) configured to image a volume where one or more medical instruments are deployed. A registration module (136) registers two images of the one or more medical instruments to compute a transform between the two images, the two images being separated in time. A planning module (142) is configured to have positions of the volume and the one or more medical instruments updated based on the transform and, in turn, update a treatment plan in accordance with the updated positions such that changes in the volume and positions of the one or more medical instruments are accounted for in the updated plan.

19 Claims, 3 Drawing Sheets

(51) Int. Cl.
 *G16H 50/50*  (2018.01)
 *A61N 5/10*  (2006.01)
 *A61B 34/20*  (2016.01)

(52) U.S. Cl.
 CPC .......... *A61N 5/1038* (2013.01); *G16H 50/50* (2018.01); *A61B 2034/2051* (2016.02); *A61B 2034/2055* (2016.02); *A61B 2034/2061* (2016.02); *A61B 2034/2065* (2016.02); *A61B 2090/378* (2016.02); *A61N 5/1067* (2013.01)

(58) Field of Classification Search
 CPC ... A61B 2090/378; A61B 34/10; A61B 90/06; A61N 5/1027; A61N 5/1038; A61N 5/1067; G16H 50/50
 See application file for complete search history.

(56) References Cited

U.S. PATENT DOCUMENTS

| | | | |
|---|---|---|---|
| 7,942,931 | B2 | 5/2011 | Gonzalez |
| 8,790,234 | B2 | 7/2014 | Price |
| 9,345,387 | B2 * | 5/2016 | Larkin ............... A61B 1/00087 |
| 9,533,173 | B2 | 1/2017 | Manzke |
| 9,555,263 | B2 | 1/2017 | Groke |
| 9,980,630 | B2 | 5/2018 | Larkin |
| 10,029,120 | B2 | 7/2018 | Schulz |
| 10,143,852 | B2 | 12/2018 | Bharat |
| 10,279,194 | B2 | 5/2019 | Bharat |
| 2004/0228509 | A1 * | 11/2004 | Holupka ............... A61N 5/1027 382/128 |
| 2013/0102891 | A1 | 4/2013 | Binnekamp et al. |
| 2013/0204072 | A1 | 8/2013 | Verard et al. |
| 2015/0011875 | A1 * | 1/2015 | Noordhoek ............ A61B 6/035 600/426 |
| 2015/0119628 | A1 | 4/2015 | Bharat et al. |
| 2016/0000519 | A1 | 1/2016 | Dehghan Marvast |

FOREIGN PATENT DOCUMENTS

| | | | | |
|---|---|---|---|---|
| WO | WO2012001551 | * | 5/2012 | ............... A61N 5/10 |
| WO | WO2013171615 | * | 11/2013 | ............... A61N 5/10 |
| WO | 2016059603 A1 | | 4/2016 | |

OTHER PUBLICATIONS

Pennec, X., et a;, "Understanding the "Demon's Algorithm": 3D Non-rigid Registration by Gradient Descent", Proc: Medical Image Computing and COmputer Assisted Intervention (MICCAI'99), LNCS 1679, pp. 597-606, 1999.

* cited by examiner

ADAPTIVE PLANNING AND DELIVERY OF HIGH DOSE RATE BRACHYTHERAPY

CROSS-REFERENCE TO PRIOR APPLICATIONS

This application is the U.S. National Phase application under 35 U.S.C. § 371 of International Application Serial No, PCT/IB2015/059429, filed on Dec. 8, 2015, which claims the benefit of U.S. Application Ser. No. 62/090,536, filed on Dec. 11, 2014. These applications are hereby incorporated by reference herein.

BACKGROUND

Technical Field

This disclosure relates to medical instruments and more particularly to systems and methods for adaptive planning and procedure updating, e.g., for high dose rate (HDR) brachytherapy or other procedures, using image based techniques.

Description of the Related Art

High Dose Rate (HDR) brachytherapy is a treatment for prostate cancer in which some radioactive sources are temporarily introduced into the prostate gland through several hollow catheters to kill the cancerous tissue. In ultrasound (US) guided HDR brachytherapy, the hollow catheters are implanted inside the prostate, based on a plan, by passing the catheters through a guiding grid. Then, a three-dimensional (3D) US volume is generated by translating a Transrectal Ultrasound (TRUS) probe from base to apex. The prostate and the catheters are segmented on the images, and the position of the catheters is sent to a computer, which optimizes a location of the radioactive sources inside the catheters (dwell positions) and the amount of time (dwell time) that the radioactive source should be present at the dwell positions. A plan is then executed using an afterloader. A drawback of this approach is that catheter segmentation in US images is cumbersome and difficult due to shadowing and calcifications.

Electromagnetic (EM) trackers have been proposed to localize the catheters. In this type of system, a probe is tracked with an EM-tracker to create a 3D ultrasound volume by retraction of the probe from prostate base to apex. Also, the guiding grid is related to the ultrasound volume using an EM tracked pointer in a calibration phase. The relationship between EM trackers and the ultrasound volume is known after the calibration phase. After insertion of the catheters, an EM-tracked guide-wire is inserted through the catheters to localize them in the ultrasound volume.

Even after careful calibration, there is some error between the catheter's locations identified using EM-tracking and the real position of the catheters that appears as bright regions in the ultrasound volume. If not corrected, this error can result in significant under- or over-dosage of the tissue. Reasons for this error can be a result of an original calibration error between the US image and the probe EM tracker and also variations in the magnetic field of the EM field-generator caused by metallic objects nearby, or simply by changes in the readings of the EM trackers caused by different distances and/or orientation of a field-generator. In another method, ultrasound tracking technology may be employed to localize the catheters.

When the plan is transferred to the afterloader, the afterloader sequentially inserts the radioactive sources inside the catheters to irradiate the tissue based on the plan. The total radiation time can reach about half an hour. During this time, the patient or catheters may move. In addition, the prostate swells as a result of catheter insertion trauma and also radiation. Therefore, the relative position of the catheters with respect to the prostate can change during the radiation. In current practice, none of these factors are taken into account.

SUMMARY

In accordance with the present principles, a system for dynamic localization of medical instruments includes an ultrasound imaging system configured to image a volume where one or more medical instruments are deployed. A registration module is configured to register at least two images of the one or more medical instruments to compute a transform between the at least two images, the at least two images being separated in time. A planning module is configured to have positions of the volume and the one or more medical instruments updated based on the transform and, in turn, update a treatment plan in accordance with the updated positions such that changes in the volume and positions of the one or more medical instruments are accounted for in the updated plan.

Another system for dynamic localization of medical instruments includes a tracking system configured to track a position of one or more medical instruments, a guidance grid configured to receive the one or more medical instruments to assist in positioning the one or more medical instruments when deployed in a volume and an ultrasound imaging system configured to image the volume where one or more medical instruments are deployed. A registration module is configured to register at least two images of the one or more medical instruments to compute a transform between the at least two images, the at least two images being separated in time. A planning module is configured to have positions of the volume and the one or more medical instruments updated based on the transform and, in turn, update a treatment plan during treatment in accordance with the updated positions such that changes in the volume and positions of the one or more medical instruments are accounted for in the updated plan.

A method for dynamically localizing medical instruments includes tracking positions of the one or more medical instruments in a volume; ultrasonically imaging the one or more medical instruments in the volume at a first instance where the one or more medical instruments are deployed; ultrasonically imaging the one or more medical instruments in the volume at a subsequent instance during treatment where the one or more medical instruments are deployed; registering the volume in the first instance with the volume in a subsequent instance to compute a transformation between images of the volume in the first instance and the volume in the subsequent instance; updating positions of the one or more medical instruments and organs in the volume between the images using the transformation; updating the positions in a planning module; and updating a treatment plan using updated positions.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
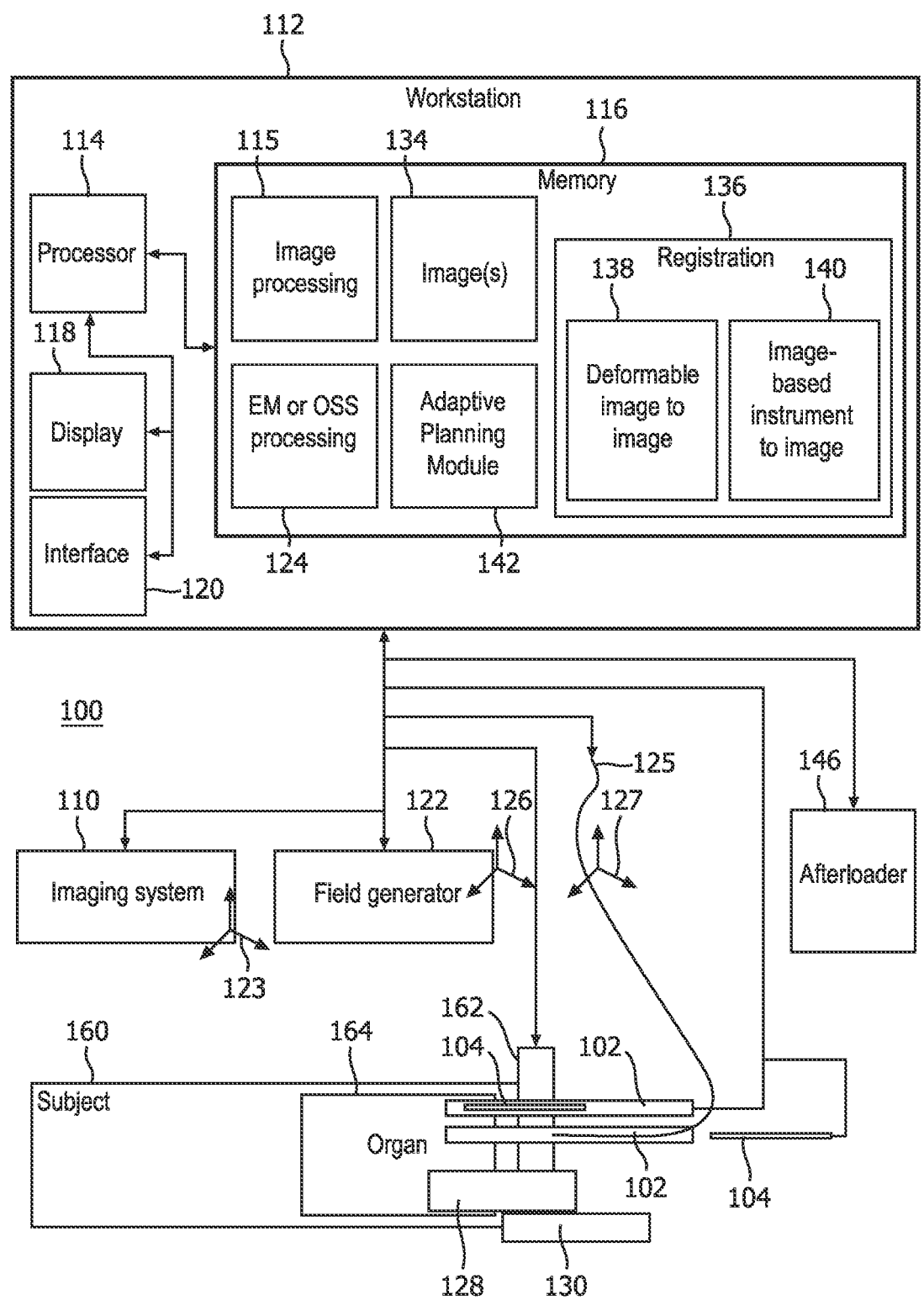
FIG. 1 is a block/flow diagram showing a dynamic system for instrument localization using ultrasound images in accordance with one embodiment.

In accordance with the present principles, systems and methods for automatic localization of medical instruments, such as catheters or needles, in ultrasound (US) are provided that account for variables that may occur that are not presently considered. In accordance with particularly useful embodiments, adaptive planning is employed for high dose rate (HDR) prostate brachytherapy. Since a radioactive source is introduced into catheters sequentially, it is possible to adapt a plan before inserting the source into each catheter. The changes in prostate volume, prostate or catheter positions and other effects (movements, etc.) can be taken into account before or during tissue irradiation. This can, in turn, improve the conformity of dose coverage and increase the treatment quality. An image-based registration method is employed to register positions of the catheters in an image coordinate system (e.g., an ultrasound coordinate system).

High Dose Rate (HDR) brachytherapy is a treatment for prostate cancer through internal radiation temporarily provided by some radioactive sources that pass through hollow catheters inserted into the prostate. Accurate localization of the catheters with respect to the prostate anatomy is needed for accurate planning and dose delivery. Catheters are digitized once prior to a procedure and a plan is devised to deliver a sufficient dose to the target gland yet spare the other organs. The plan is then transferred to an afterloader system that inserts the radioactive sources inside the catheters based on the plan. In conventional practice, the plan is not adapted once radiation treatment has begun. However, the patient may move during the radiation or the prostate will swell as a response to radiation and trauma of catheter insertion. Therefore, the position of the catheters with respect to the prostate may change during the irradiation.

The present principles provide ultrasound-guided adaptive HDR planning to detect and correct for changes in prostate position and volume. The ability to adapt the plan for HDR prostate brachytherapy can be an important feature in any multi-modality brachytherapy system. HDR-specific adaptive workflows in accordance with useful embodiments permit changes after radiation treatment has begun to fine-tune execution of a treatment plan. Deformable image registration of multiple US volumes and image-based registration may be employed to register tracked representations of catheters to an US image. Tracking technology may be employed to detect the changes in position and volume of the prostate and any catheter movements. This information is passed on to a processing unit for intraoperative adaptive planning for HDR brachytherapy. In one embodiment, a 3D transrectal US (TRUS) probe is employed for imaging the prostate during the delivery of radiation. Before the radioactive capsule is inserted into a new catheter, a new 3D US volume is acquired. The new volume is deformably registered to the previous volume or a base-line volume. The deformable registration reveals the new position and volume of the prostate and other critical structures. Also, the position of the catheters digitized in previous volumes can be transferred to the new volume using the deformable image registration results. In addition, the new position of the catheters can be measured using tracking technologies. The information is fed into a computer system to adapt the plan accordingly.

It should be understood that the present invention will be described in terms of medical instruments; however, the teachings of the present invention are much broader and are applicable to any imaging system. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, prostate, kidneys, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for adaptive localization of medical instruments and planning using ultrasonic images is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an image processing module 115 configured to interpret and compare images from an ultrasonic imaging system 110. Image processing module 115 is configured to collect or receive images obtained using a US probe 128. The US probe 128 may include a transrectal US (TRUS) probe (2D or 3D) as the present principles will be illustratively described in terms of a high-dose-rate (HDR) brachytherapy procedure. The probe 128 may employ an optically tracked US probe, an electromagnetic (EM)-tracked US probe, a non-tracked 3D probe, etc. The image processing module 115 may also be employed to provide functions such as manual or automatic digitization of instruments and/or organs in an imaging volume or image 134.

During a procedure, medical instruments 102, such as catheters, applicators or other instruments are inserted into a subject 160 (e.g., a patient) and in particular an organ 164 such as a prostate, etc. In a brachytherapy application, the instruments 102 may pass through a guidance grid 162. The guidance grid 162 may be calibrated/registered with a coordinate system 123 of the imaging system 110 in advance of a procedure (i.e., a priori). The instruments 102 may be configured to include or receive tracking devices 104 therein, e.g., EM tracking, optical shape sensing devices/systems, etc. The catheters 102, which are hollow tubes, are inserted into the tissue (subject 160 or organ 164). Then, a shape reconstructing device or tracking device 104, such as an EM-tracked guidewire or an optical shape sensing fiber is inserted into the catheters 102 and removed. In fact, one EM-tracked guidewire or optical shape sensing (OSS) fiber 125 can be used to reconstruct the shape of several catheters. In other embodiments, the catheters 102 and the shape-reconstructing sensors (125) or tracking devices 104 may also be integrated together. It should be understood that other procedures, such as image-based registration and tracking may be employed as well.

For EM tracking, in one illustrative embodiment, positions of the instruments 102 are tracked using a field generator 122 and a tracking system processing module 124 (e.g., for EM tracking). The EM field is generated, and the movements of the instruments 102 are tracked in an EM coordinate system 126. For OSS fiber tracking, in one illustrative embodiment, positions of the instruments 102 are tracked using feedback from a fiber optic device 125 and the tracking system processing module 124 (e.g., for optical shape sensing). The module 124 may include separate modules for EM tracking and OSS tracking, but has been depicted as a single module for ease of reference. The back reflected light generated by the shapes of the fiber device is tracked in its own coordinate system (e.g., a coordinate system 127). While only a single tracking method is needed, multiple systems may be employed together, or other tracking systems may be employed.

In accordance with one embodiment, an image-based approach can be used to overlay or register the catheter positions from the EM processing module 124 onto the US volume in the image processing module 115 using a registration module 136, and, hence, localize the catheters 102 in the US volume. In other embodiments, the EM processing may be replaced with optical shape sensing in module 124, and the EM tracking devices 104 may be replaced by optical fibers for shape sensing. EM signals or optical signals are employed to determine the positions of the instruments 102. The instruments 102 preferably include catheters but may include a guidewire, a probe, an endoscope, other medical component, etc.

Other registration systems and techniques may also be employed. For example, image based registration is one way of registering the digitized catheters to a US volume. If the catheters are manually digitized in the image or digitized using instrument tracking using US (InSitu), they are already in the US coordinate system and registration is not necessary. If the probe 128 is tracked using OSS or EM and the catheters 102 are digitized in the same way registration can be done using tracking information without relying on the image.

It should be understood that understanding the positions of organs and/or medical devices within or near the organs can be conducted in a plurality of different ways in accordance with the present principles. For example, 3D sequential deformable image registration (image to image) 138 may be employed to track overall organ, contours, etc. This can be done without any tracking of probes or catheters. In this way, everything can be done by image-based registration and with manual identification of catheters (102) at least in a first image (or possibly automatic image-based catheter identification). This uses the probe 128, e.g., a volumetric ultrasound probe or a 2D US probe, whose position is known due to a stepper 130 on which the probe 128 and/or grid 162 are actuated, i.e., with active or passive position encoding of the stepper 130, so a 3D US image can be reconstructed.

With spatial tracking, a 2D ultrasound probe 128 may be employed to facilitate reconstruction of the 3D US. The probe 128 may be tracked using, e.g., EM, OSS, optical or other tracking mechanism (or simply the mechanical active/passive position encoding of the stepper 130). With spatial tracking or "mapping" of the catheters 102, a one-time only mapping (right after insertion) followed by image-based propagation of the catheter shapes/positions to subsequent images is performed or an intermittent mapping is performed throughout the procedure (e.g., for each 3D US that is acquired, or for every nth image) by instrument to image based registration module 140 (also a form of deformable image registration). The spatially tracked catheter shapes may or may not need registration to the latest 3D US image.

For intelligent sensing for instrument tracking using US (InSitu) the instruments 102 are always registered to ultrasound, though there may be benefits from re-registration to the image, e.g., "path to volume" registration may provide better accuracy than just using the InSitu "as is".

OSS and EM tracking may be employed as described. This is especially advantageous if the probe 128 is tracked with the same tracking modality as the tracking system, then similarly to InSitu, the location of the tracked paths would also be known in US coordinates (subject to calibration, tracking errors, etc.), but may still benefit from re-registration ("path-to-image") for better accuracy. If the probe is not tracked with the same modality, then the tracked path needs to be registered to the latest image.

In one embodiment, workstation 112 includes a display 118 for viewing internal images of the subject (patient) 160 and may include the image 134 of the volume as an overlay of another image or rendering. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

Memory 116 may store the registration module 136, which preferably includes a deformable image registration module 138 for registering multiple US volumes (e.g., track changes over time). The registration module 136 includes an image-based registration module 140 to register tracked representations of catheters to an US image or images 134. The tracked representation may include image-based tracking, EM, OSS, InSitu or other tracking technology for ultrasound image registration.

Memory 116 also includes an adaptive planning module 142 for planning a procedure, such as an HDR prostate brachytherapy procedure or the like. The planning module or planner 142 computes dwell positions and times using catheter positions and delineations of organs of interest in the ultrasound coordinate system as part of the plan or at any time during the procedure to update the plan. The dose and amount of dwell time may be computed for high dose rate (HDR) brachytherapy or any other procedure. One benefit of the registration methods employed is that after the registration, both catheters and the organ contours can be in the same coordinate system and can be used for tracking progress.

The present principles provide ultrasound-guided adaptive HDR planning to detect and correct for changes in organ position and volume. The ability to adapt the plan for HDR prostate brachytherapy can be an important feature in any multi-modality brachytherapy system. HDR-specific adaptive workflows in accordance with useful embodiments permit changes after radiation treatment has begun to fine-tune execution of a treatment plan. Deformable image registration module 138 and image-based registration module 140 may be employed to register representations of instruments (catheters) 102 to the US image 134.

Tracking technology may be employed to detect the changes in position and volume of the prostate and any catheter movements over time. Tracking as in EM or OSS cannot be used to detect the changes in the position and volume of the organs, e.g., the prostate. The deformable image registration module 138 gives information about the changes in the location or volume of the organ(s). To update the position of the catheters 102, a tracking technology (EM, OSS, etc.) or the deformable image registration can be relied upon.

The change information is passed on to the planner 142 for intraoperative adaptive planning for HDR brachytherapy or other procedure. In one embodiment, a 3D transrectal US (TRUS) probe (128) is employed for imaging a prostate (164) during the delivery of radiation. Before a radioactive capsule is inserted into a new catheter, a new 3D US volume is acquired. The new volume is deformably registered to the previous volume or a base-line volume. The deformable registration provided by module 138 reveals the new position and volume of the prostate and other critical structures. Also, the position of the catheters digitized in previous volumes can be transferred to the new volume. In addition, the new position of the catheters can be measured using tracking technologies. The information is fed into the workstation 112 and in particular the planning module 142 to adapt the plan accordingly.

The treatment plan is sent to an afterloader 146, which then controls the delivery of radioactive sources along the guide tubes into the pre-specified positions within the catheters 102. The sources remain in place for a pre-specified dwell time, following the treatment plan. The sources are returned along the tubes to the afterloader 146.

Different embodiments described herein may employ, some or all of the elements of FIG. 1 as needed. The registration module 136 and planning module 142 as well as other components in FIG. 1 will be described in greater detail with reference to FIGS. 2 and 3.

Figure 2:
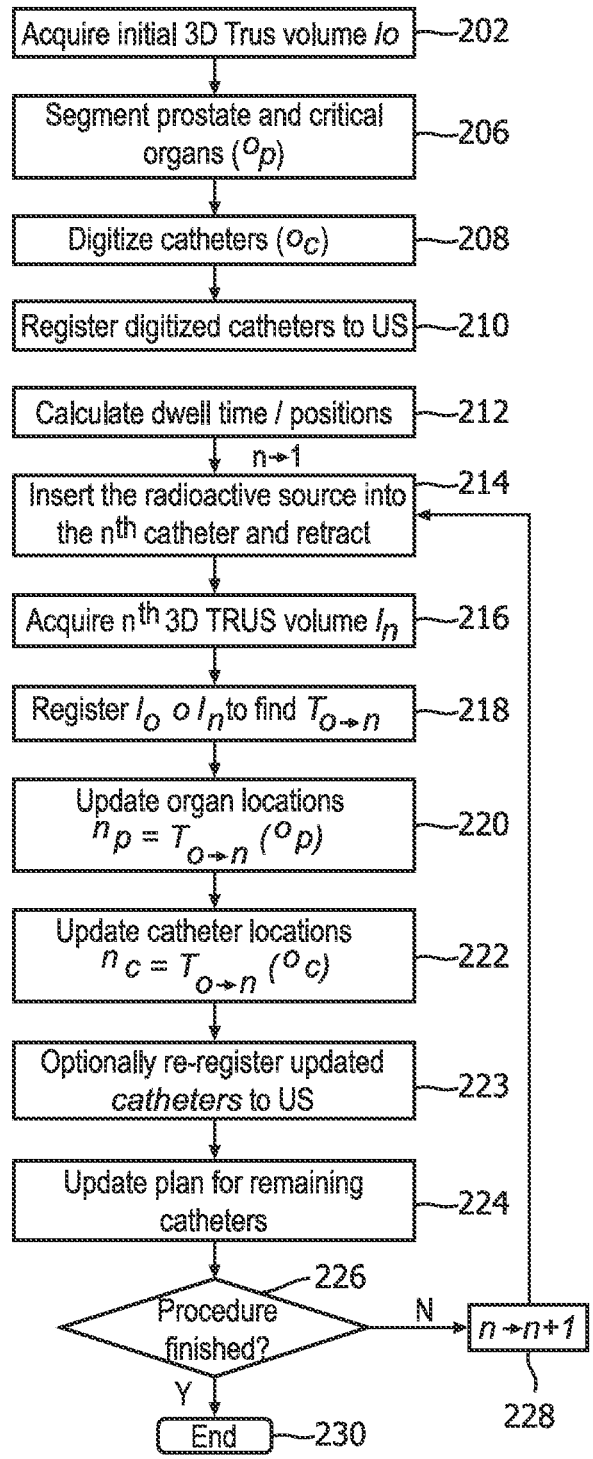
FIG. 2 is a flow diagram showing a method for dynamic instrument localization and planning in accordance with one illustrative embodiment.

Referring to FIG. 2, a flow diagram shows the present principles integrated into a clinical workflow for adaptive planning for HDR prostate brachytherapy, using a base-line image. In the embodiment of FIG. 2, in each step a new ultrasound volume (n) is registered to a first ultrasound volume (n−1). Assume that that a patient is prepped for a procedure in an operating room and all the necessary catheters are inserted into his prostate or other organ. Following the insertion of all the catheters, the following tasks are performed. In block 202, a 3D ultrasound volume is acquired as a baseline volume. The volume can be acquired using a stationary 3D TRUS probe or by retraction or rotation of a tracked 2D TRUS probe. The 2D TRUS probe can be tracked using EM, OSS or on a brachytherapy stepper that has translational and rotational encoders. The 3D probe can also be tracked. The image (134, FIG. 1) or volume is designated as: $I_0$.

In block 206, a target (prostate, in this case) and other critical organs such as a bladder, urethra, rectum, etc. may be contoured (segmented) in the US volume, $I_0$. The position of these structures in the ultrasound coordinate system is designated as: $p_{US}$ or $^0p$. The catheters are digitized in block 208 and their positions ($^0c$) are registered to the US volume in block 210. Inserted catheters are digitized in the US volume. Catheter digitization can be done by a plurality of methods. These may include manual segmentation, electromagnetic (EM) tracking, Intelligent sensing for instrument tracking using US (e.g., InSitu tracking), optical shape sensing (OSS), etc. The digitized catheters are registered to the ultrasound volume, $I_0$. The position of the catheters in a tracker coordinate system (126, FIG. 1) is $c_{Tr}$ and their position in a US coordinate system (138, FIG. 1) is $c_{US}$, such that $c_{US}=T_{Tr \to US} * c_{Tr}$. If the catheters are digitized manually or using InSitu technology, they are already registered to the US volume and identification of $T_{Tr \to US}$ is not necessary. If a tracking technology is employed (e.g., EM, OSS, etc.), tracked ultrasound or image-based registration can be used to identify $T_{Tr \to US}$.

The organ locations (and/or contours) and the registered digitized catheters are passed to the planning module 142 (FIG. 1) to determine dwell positions and dwell times of radioactive sources along each catheter in block 212. The plan is transferred to the afterloader (146, FIG. 1). Afterloading involves loading the radiation sources. The afterloader places the radioactive sources inside the catheters. In this stage the non-radioactive catheters or applicators are already at the treatment site. Remote afterloading systems provide protection from radiation exposure to healthcare professionals by securing the radiation source in a shielded safe. Once the catheters are correctly positioned in the patient, they are connected to the afterloader (having the radioactive sources) through a series of connecting guide tubes. The treatment plan is sent to the afterloader, which then controls the delivery of the sources along the guide tubes (catheters) into the pre-specified positions within the catheters. The sources remain in place for a pre-specified dwell time, following the treatment plan. The sources are returned along the tubes to the afterloader. A first source is inserted into a first catheter and left for a dwell time and then retracted in block 214.

After the source is retracted from the first catheter, a new ultrasound volume, $I_n$, is acquired in block 216. This new US volume can be acquired, e.g., using the stationary 3D probe or a tracked 2D one.

In block 218, the new ($I_n$) and old ($I_0$) ultrasound volumes are deformably registered using variations of, e.g., the Demon's registration algorithm or other registration algorithm. The transformation from the old ultrasound volume ($I_o$) to the new one ($I_n$) is $T_{0 \to n}$ (or $T_{0 \to 1}$). The deformable registration is performed by the deformable image registration module 138 (FIG. 1).

In block 220, the positions of the target and other critical organs are updated to the current ultrasound coordinate system as: $^n p_{US} = T_{0 \to n}(^0 p_{US})$. In block 222, the catheter positions are updated. In one embodiment, the catheter positions can be updated using the transformation calculated in block 218 such that: $^n c_{US} = T_{0 \to n}(^0 c_{US})$. In another embodiment, the next catheter can be re-digitized in the new ultrasound volume using tracking methods such as EM, OSS, ultrasound tracking technology, etc. and the rest of the catheters are updated using the transformation from block 218. In yet another embodiment, the rest of the catheters can be re-digitized in the new ultrasound volume using tracking methods such as EM, OSS, ultrasound tracking technology, etc.

In block 223, the position of the newly digitized catheter can also be re-registered to the newly acquired ultrasound volume using an image based registration method, etc., if necessary. The re-registration is optional. Note that the new digitized catheter can be registered to the US volume using any of the registration methods described above with reference to FIG. 1. Image-based registration is one of the possibilities. Since the initially digitized catheters are registered to $I_0$ and $I_0$ is registered to $I_n$, in case of tracked probe or stationary 3D probe or InSitu tracking, the newly digitized catheter is already registered, and a new registration may be redundant. However, a re-registration can increase accuracy.

In this method, first the locations of all the catheters are updated based on the deformable registration method (module 138, FIG. 1). Then, the position of the newly tracked catheter is locally optimized using the image-based registration method (using the image-based registration module 140, FIG. 1). In another embodiment, all the catheters can be re-digitized using the tracking methods such as EM, OSS, InSitu, etc. and registered to the new ultrasound volume. The positions of the re-digitized catheters can be registered to the newly acquired ultrasound volume using image-based registration (image-based registration module 140, FIG. 1) or other tracking method.

In block 224, the updated catheter positions and the updated organ positions are transferred to the planning module 142 (FIG. 1) to update the plan. The new plan is transferred to the afterloader to insert a radioactive source in a new catheter. After the retraction of the source from the catheter, the above steps from block 214 are repeated. In the embodiment of FIG. 2, in each step, the new ultrasound volume is registered to the first ultrasound volume. In this case for volume n, in blocks 214, 216 and 218, the superscript or the subscript is "n". In block 226, a check is performed to determine if the plan is fully executed. If the plan is not complete, a step is advanced (n becomes n+1) in block 228, and the process returns to block 214 to further carry out the plan. If the plan has been completed, the process ends in block 230.

Figure 3:
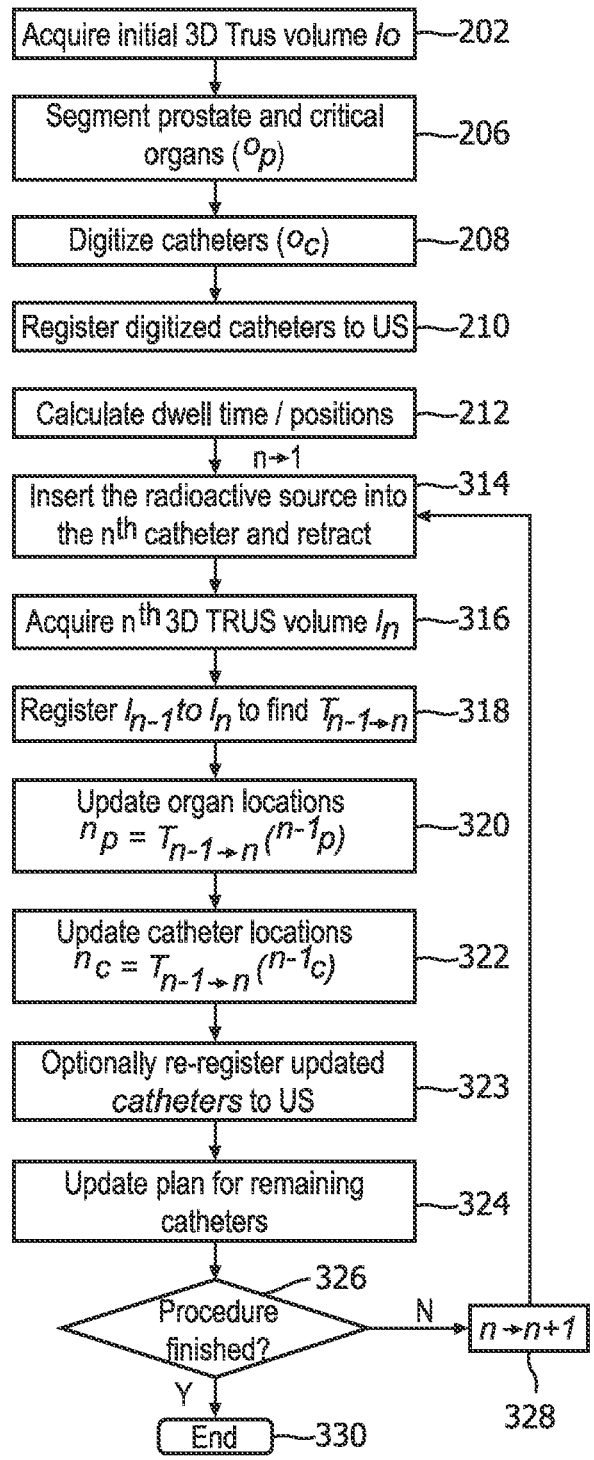
FIG. 3 is a flow diagram showing another method for dynamic instrument localization and planning in accordance with another illustrative embodiment.

Referring to FIG. 3, a flow diagram shows the present principles integrated into a clinical workflow for adaptive planning for HDR prostate brachytherapy, using an incrementally updated image approach. In the embodiment of FIG. 3, in each step a new ultrasound volume (n) is registered to a previous volume (n−1) and the updates are incremental. In blocks 314, 316 and 318, the superscript or the subscript "0" in the equations in FIG. 2) is replaced by "n−1". Assume that that a patient is prepped for a procedure in an operating room and all the necessary catheters are inserted into his prostate or other organ. Following the insertion of all the catheters, the following tasks are performed. Blocks 202-212 are performed in essentially the same manner as described with respect to FIG. 2.

As before, the plan is transferred to the afterloader (146, FIG. 1). A first source is inserted into a first catheter and left for a dwell time and then retracted in block 314.

After the source is retracted from the first catheter, a new ultrasound volume, $I_n$, is acquired in block 316. In block 318, the new ($I_n$) and old ($I_{n-1}$) ultrasound volumes are deformably registered using variations of, e.g., the Demon's registration algorithm or other registration algorithm. The transformation from the old ultrasound volume ($I_{n-1}$) to the new one ($I_n$) is $T_{n-1 \to n}$ (or $T_{0 \to 1}$). The deformable registration is performed by the deformable image registration module 138 (FIG. 1).

In block 320, the positions of the target and other critical organs are updated to the current ultrasound coordinate system as: $p_{US} = T_{n-1 \to n}(^{n-1} p_{US})$. In block 322, the catheter positions are updated. In one embodiment, the catheter positions can be updated using the transformation calculated in block 318 such that: $^n c_{US} = T_{n-1 \to n}(^{n-1} c_{US})$. In another embodiment, the next catheter can be re-digitized in the new ultrasound volume using tracking methods such as EM, OSS, InSitu, etc. and the rest of the catheters are updated using the transformation from block 318. In yet another embodiment all the remaining catheters can be re-digitized using tracking methods such as EM, OSS, InSitu, etc. The position of the newly digitized catheter can be registered to the newly acquired ultrasound volume using an image based registration method or any other tracking or registration method.

In this method, first the locations of all the catheters are updated based on the deformable registration method (module 138, FIG. 1). Then, the position of the newly tracked catheter is locally optimized using the image-based registration method (using the image-based registration module 140, FIG. 1). In another embodiment, all the catheters can be re-digitized using the tracking methods such as EM, OSS, InSitu, etc. and registered to the new ultrasound volume. The positions of the re-digitized catheters can be registered to the newly acquired ultrasound volume using an image-based registration (image-based registration module 140, FIG. 1) or other method, as described. In block 323, the position of the newly digitized catheter can also be re-registered to the newly acquired ultrasound volume using an image based registration method, etc., if necessary. The re-registration is optional.

In block 324, the updated catheter positions and the updated organ positions are transferred to the planning module 142 (FIG. 1) to update the plan. The new plan is transferred to the afterloader to insert a radioactive source in a new catheter. After the retraction of the source from the catheter, the above steps from block 314 are repeated. In the embodiment of FIG. 3, in each step, the new ultrasound volume is registered to the previous ultrasound volume (n−1), in blocks 314, 316 and 318. In block 326, a check is performed to determine if the plan is fully executed. If the plan is not complete, a step is advanced (n becomes n+1) in block 328, and the process returns to block 314 to further carry out the plan. If the plan has been completed, the process ends in block 330.

In accordance with the above methods, before a radioactive capsule is inserted into a new catheter, a new 3D US volume is acquired. The new volume is deformably registered to a base-line volume (FIG. 2) or to a previous volume (FIG. 3). The deformable registration reveals a new position and volume of the prostate, organ or other structures. Also, the position of the catheters digitized in previous volumes can be transferred to the new volume. In addition, the new position of the catheters can be measured using tracking technologies. The information is fed into a computer system to adapt the plan accordingly.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for adaptive planning and delivery of high dose rate brachytherapy (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for dynamic localization of one or more medical instruments, comprising:
 a tracking system configured to track positions of the one or more medical instruments in a tracking coordinate system;
 a guidance grid configured to receive the one or more medical instruments to assist in positioning the one or more medical instruments when configured to be deployed in a volume;
 an ultrasound imaging system configured to image the volume when the one or more medical instruments are configured to be deployed in the volume in an ultrasound imaging coordinate system, the image of the volume depicting a position of at least one organ in the volume;
 one or more processors configured to:
  register the positions of the one or more medical instruments in the tracking coordinate system to the ultrasound imaging coordinate system,
  register the guidance grid to the ultrasound imaging coordinate system,
  control the ultrasound imaging system to generate at least two images including a prior ultrasound image and a current ultrasound image of the volume when the one or more medical instruments are configured to be deployed in the volume, the at least two images being separated in time,
  compute a transformation between the prior and current images in the ultrasound imaging coordinate system by deformably registering from the prior ultrasound image to the current ultrasound image,
  transform:
   the position in the ultrasound imaging coordinate system of the at least one organ in the volume with the transformation, and
   a position of the one or more medical instruments in the volume with the transformation, and
  update a treatment plan during treatment of the at least one organ in accordance with the transformed positions of the at least one organ and the one or more medical instruments such that changes over time in the positions of the at least one organ and of the one or more medical instruments are accounted for in the updated treatment plan.

2. The system as recited in claim 1, wherein the tracking system tracks the one or more medical instruments using at least one of manual digitization, electromagnetic tracking, optical shape sensing, intelligent sensing using ultrasound or image based tracking.

3. The system as recited in claim 1, wherein the one or more medical instruments comprise one or more catheters or one or more applicators configured for receiving radioactive sources therein for delivering treatment to an organ.

4. The system as recited in claim 1, wherein the updates to the treatment plan account for at least one of patient movement, organ swelling or movement, or placement error.

5. The system as recited in claim 1, wherein the ultrasound imaging system comprises a transrectal ultrasonic (TRUS) probe, and the one or more medical instruments include one or more catheters for deploying radiation sources for brachytherapy.

6. The system as recited in claim 1, wherein the one or more processors is further configured to determine locations of the one or more organs and the one or more medical instruments and determine a difference in the positions over time.

7. The system as recited in claim 1, wherein the transformation computed by the one or more processors is an elastic transforms.

8. The system according to claim 2, wherein the positions of the at least one medical instrument in at least one current image is also tracked by the tracking system.

9. A method for dynamically localizing a medical instrument configured to be deployed in a volume comprising:
 (a) ultrasonically imaging the volume and the medical instrument configured to be deployed therein to form a baseline image;
 (b) segmenting the baseline image to identify contours and locations of a target and organs in the volume;
 (c) digitizing a position of the medical instrument configured to be deployed in the volume with an electromagnetic instrument tracking system and registering the position of the medical instrument to the baseline image;

(d) passing the contours and locations of the target and organs and digitized positions of the medical instrument to a therapy planning system configured to calculate a first treatment position of the medical instrument in the volume to generate an initial treatment plan;

(e) treating via the medical instrument at the first treatment position (f) ultrasonically imaging the volume to form a current updated ultrasound image;

(g) determining an elastic transform between the baseline image and the updated ultrasound image by elastically registering the baseline image and the updated ultrasound image;

(h) with the elastic transform, transforming the contours and the locations of the target and the organs and the digitized position of the medical instrument from the baseline image;

(i) passing the transformed contours and locations of the target and organs and the transformed digitized position of the medical instrument to the therapy planning system for updating the treatment plan; and (j) repeating steps (f)-(i) to update the treatment plan.

10. The method as recited in claim 9, further comprising: tracking the positions of the medical instrument using at least one of electromagnetic tracking, optical shape sensing, intelligent sensing using non-ultrasound image based tracking.

11. The method as recited in claim 9, wherein the medical instrument includes at least one of one or more catheters or one or more applicators, wherein the method further comprises:
delivering treatment to the target using at least one of the one or more catheters or the one or more applicators and the updated treatment plan.

12. The method as recited in claim 9, wherein the transform accounts for at least one of patient movement, target swelling or movement, or placement error.

13. The method as recited in claim 9, further including: displaying at least one of the baseline image and the updated ultrasound image on a display device.

14. The method as recited in claim 9, further including: displaying on a display the updated ultrasound image of the volume overlaid on another image or rendering.

15. The method as recited in claim 9, wherein the medical instrument includes one or more catheters and further including:
registering a guidance grid with the ultrasound imaging coordinate system and passing the one or more catheters therethrough to guide insertion of the one or more catheters into the imaging volume.

16. A system for dynamic localization of a medical instrument configured to be deployed in a volume of a patient, comprising:
an electromagnetic (EM) tracking system configured to track positions of the medical instrument in the volume in a tracking coordinate system;
an ultrasound imaging system configured to image the volume when the medical instrument is configured to be deployed in the volume in an ultrasound imaging coordinate system, the image of the volume depicting a position of at least one organ and a target in the ultrasound imaging coordinate system; and
one or more processors configured to:
(a) control the ultrasound imaging system to generate a baseline ultrasound image of the volume,
(b) segment the baseline ultrasound image to identify contours and locations of a target and organs in the volume,
(c) digitize a position of the medical instrument configured to be deployed in the volume with the EM tracking system and register the position of the medical instrument to the baseline image,
(d) pass the target and the organ contours and location and the digitized position of the medical instrument to a therapy planning system configured to generate an initial treatment plan including a first treatment position of the medical instrument in the volume,
(e) control the medical instrument to perform a treatment at the first treatment position,
(f) ultrasonically image the volume to form an updated ultrasound image of the volume,
(g) determine an elastic transform between the baseline image and the updated ultrasound image,
(h) transform the contours and locations of the target and the organs and the digitized position of the medical instrument from the baseline image,
(i) digitize an updated position of the medical instrument with the EM tracking system and register the position of the medical instrument to the updated ultrasound image,
(j) pass to the therapy planning system:
the elastically transformed contours and locations of the target and the organs and the digitized position of the medical instrument from the updated ultrasound image, and
the updated digitized position of the medical instrument from the EM tracking system, and
updating the treatment plan,
(k) repeating steps (f)-(j) to repeatedly update the treatment plan.

17. The system according to claim 16, further including a display device and wherein the one or more processors are further configured to:
control the display device to display at least one of the baseline ultrasound image, the updated ultrasound image, and the updated ultrasound image overlaid on another image or rendering including the volume.

18. A method for dynamically localizing a medical instrument configured to be deployed in a volume comprising:
(a) receiving an ultrasonic image of the volume and the medical instrument configured to be deployed therein as a baseline image;
(b) segmenting the baseline image to identify contours and locations of a target and organs in the volume;
(c) digitizing a position of the medical instrument configured to be deployed in the volume with an electromagnetic instrument tracking system and registering the position of the medical instrument to the baseline image;
(d) calculating a treatment position of the medical instrument in the volume to generate a treatment plan;
(f) receiving, as an updated ultrasound image, an ultrasonic image of the volume after an execution of the treatment plan;
(g) determining an elastic transform between the baseline image and the updated ultrasound image by elastically registering the baseline image and the updated ultrasound image;

(h) with the elastic transform, transforming the contours and the locations of the target and the organs and the digitized position of the medical instrument from the baseline image;
(i) updating the treatment plan; and
(j) receiving, as another updated ultrasound image, an ultrasonic image of the volume after an execution of the updated treatment plan;
(g) determining an elastic transform between the baseline image and the another updated ultrasound image by elastically registering the baseline image and the another updated ultrasound image;
(h) with the elastic transform, transforming the contours and the locations of the target and the organs and the digitized position of the medical instrument from the baseline image; and
(i) updating the updated treatment plan.

19. A system for dynamic localization of a medical instrument configured to be deployed in a volume of a patient, comprising:
one or more processors configured to:
(a) receive a baseline ultrasound image of the volume,
(b) segment the baseline ultrasound image to identify contours and locations of a target and organs in the volume,
(c) digitize a position of the medical instrument configured to be deployed in the volume with the EM tracking system and register the position of the medical instrument to the baseline image,
(d) generate an initial treatment plan including a first treatment position of the medical instrument in the volume,
(f) ultrasonically image the volume to form an updated ultrasound image of the volume,
(g) determine an elastic transform between the baseline image and the updated ultrasound image,
(h) transform the contours and locations of the target and the organs and the digitized position of the medical instrument from the baseline image,
(i) digitize an updated position of the medical instrument with the EM tracking system and register the position of the medical instrument to the updated ultrasound image,
(j) update the treatment plan; and
(k) repeating steps (f)-(j) to further update the treatment plan.

\* \* \* \* \*